United States Patent [19]

Trentham et al.

[11] 4,152,129

[45] May 1, 1979

[54] METHOD FOR SEPARATING CARBON DIOXIDE FROM METHANE

[75] Inventors: Harold L. Trentham; Arnold M. Hegwer, both of Houston, Tex.

[73] Assignee: Trentham Corporation, Houston, Tex.

[21] Appl. No.: 765,432

[22] Filed: Feb. 4, 1977

[51] Int. Cl.$^2$ ................................................. F25J 3/02
[52] U.S. Cl. ............................................ 62/18; 62/28; 62/40
[58] Field of Search .................... 62/23, 27, 28, 18

[56] References Cited

U.S. PATENT DOCUMENTS

| | | | |
|---|---|---|---|
| 2,503,265 | 4/1950 | Haynes | 62/28 |
| 2,888,807 | 6/1959 | Bocquet | 62/23 |
| 3,290,890 | 12/1966 | Bray et al. | 62/23 |
| 3,292,382 | 12/1966 | Bray et al. | 62/23 |
| 3,376,709 | 4/1968 | Dickey et al. | 62/23 |
| 3,595,782 | 7/1971 | Bucklin et al. | 62/23 |
| 3,983,711 | 10/1976 | Solomon | 62/28 |

Primary Examiner—Norman Yudkoff
Attorney, Agent, or Firm—Pravel, Wilson & Gambrell

[57] ABSTRACT

A method is disclosed whereby carbon dioxide and methane in a gaseous mixture can be separated with little energy consumption when the gaseous mixture contains large amounts of carbon dioxide, i.e., from about 30 to about 90 mol percent. The method involves the fractionation of the gas mixture at a pressure below the critical pressure of the mixture and at a temperature above the triple point temperature of the mixture.

3 Claims, 2 Drawing Figures

METHOD FOR SEPARATING CARBON DIOXIDE FROM METHANE

BACKGROUND OF THE INVENTION

1. Field of the Invention

This invention involves the separation of carbon dioxide and methane from gaseous mixtures wherein carbon dioxide is present in large quantities, i.e., from about 30 to about 90 mol percent.

2. Discussion of the Prior Art

The presence of carbon dioxide in admixture with hydrocarbons causes the heating value of the gas mixture to be diminished. To improve the heating value of the gas mixture, carbon dioxide must be removed. A considerable number of processes are available in the recovery of natural gas for the separation of carbon dioxide from such natural gases to make them of greater use. Most of these processes involve treatment of the gases with chemicals such as amines, propylene carbonate, potassium carbonate, N-methylpyrrolidone or other solvents. These processes are limited by the amount of carbon dioxide which can be efficiently and economically removed from the gas, some of the processes being applicable to gas streams having as much as 33 molecular percent of carbon dioxide. All of these processes require that the solution absorbing the gas be recovered through a stripping operation, thus materially increasing the cost of the process through not only the use of energy, but through the loss of chemical during the stripping step. Other known processes involve molecular sieve absorption or caustic treating, but such processes all suffer from the inability to economically separate the gases when large quantities of carbon dioxide are present. Cyrogenic processes have been used for gaseous separation and U.S. Pat. No. 3,595,782 describes such a process of separating carbon dioxide from ethane to leave a waste stream containing carbon dioxide and methane. Generally, cyrogenic processes have been thought to be inapplicable to carbon dioxide separation when large amounts are present because of the great tendency for carbon dioxide to form a solid at certain conditions, thus plugging the entire system and making any method inoperable.

While equilibria data of methane and carbon dioxide binary systems are readily available and well known, those skilled in the art have heretofore been unable to arrive at an economically feasible method which either did not require great amounts of energy consumption or avoid the freezing tendency of the carbon dioxide containing systems.

Surprisingly, a method has been discovered for separating carbon dioxide and methane from a mixture which contains from about 30 to 90 mol percent carbon dioxide without excessive energy consumption or freeze-up of the carbon dioxide in the plant equipment.

SUMMARY OF THE INVENTION

It is the method of this invention to separate carbon dioxide from methane in gaseous mixtures whereby the carbon dioxide is present in an amount from about 30 to about 90 mol percent by drying the gas, if not already dry; cooling the dry gas through a series of heat exchangers wherein the heat is transferred through indirect heat exchange with various other process streams. The gas is then charged to a fractionating column wherein the methane is taken overhead and a bottoms stream consisting essentially of carbon dioxide is removed. The carbon dioxide bottom stream, being in liquid form, is used to provide initial cooling for the one portion of the incoming gas stream and further cooling for the combined incoming gas streams, principally by flashing the liquid carbon dioxide to the gas. The overhead methane stream is partially condensed, using an outside refrigerant loop, providing a liquid methane-carbon dioxide mixture for reflux to the column to improve the purity of the methane product stream and to increase the separation of methane and carbon dioxide. This methane gas product stream is also used to complete the cooling of the inlet gases and to provide partial initial cooling for the inlet gas stream through a heat exchanger and one of the inlet gas precooling streams.

The fractionation tower is operated by using side tray reboilers which receive their heat input, through indirect heat exchange, while providing cooling for the entering gas stream. There may be one or more of these side streams taken out of the fractionation vessel between various theoretical stages of the vessel, or tower.

DESCRIPTION OF THE PREFERRED EMBODIMENTS

As can be seen from the foregoing significant problems attend with respect to the separation of carbon dioxide from methane, both of which are important materials. Methane is important for its heating value and as a synthesis gas. Carbon dioxide is valuable for use to maintain pressure when producing petroleum from underground formations, and when in pure form, for other purposes. The gas mixtures treated by the method of this invention are derived through a number of ways, the principle of which is through the production of natural gas. It is not uncommon that natural gas wells having high quantities of carbon dioxide have of necessity been shut in because of the failure of previously known separation methods to be economic for the recovery of the gaseous materials. Thus, the valuable heating value of the gas is not utilized and the cost of the well is wasted. Not only are the gaseous mixtures produced naturally, they are produced synthetically through biological action on waste or by chemical reaction. Thus, it becomes advantageous to make such separation if the same can be done in an economic manner.

One problem heretofore militating against the separation of the gases has been the tendency of carbon dioxide to freeze when cryogenic separation is attempted, thus plugging the process equipment. Thus, we have discovered a method whereby such separation can be accomplished without freezing by judicious interchange of energy between various process streams while at all times maintaining the temperature of the system above the triple point temperature of the mixture and at a pressure below the critical pressure of the mixture. Once the critical pressure of the mixture is attained, separation is impossible since there is no differentiation between the liquid and vapor phase, both phases being intermixed fluids. The necessity of remaining above the triple point temperature, explained previously, is to prevent the freezing of carbon dioxide in the mixture thus causing the system to become inoperable. The following describes a method for the gas separation without large expenditure of energy, requiring but a single refrigeration system, but yet achieving substantially complete separation of the two gases even though the carbon dioxide level of the initial mixture is high, i.e., between about 30 mol percent and about 90 mol percent. The practice of this method provides methane with a greatly enhanced net heating value over that necessary to perform the method.

Figure 1:
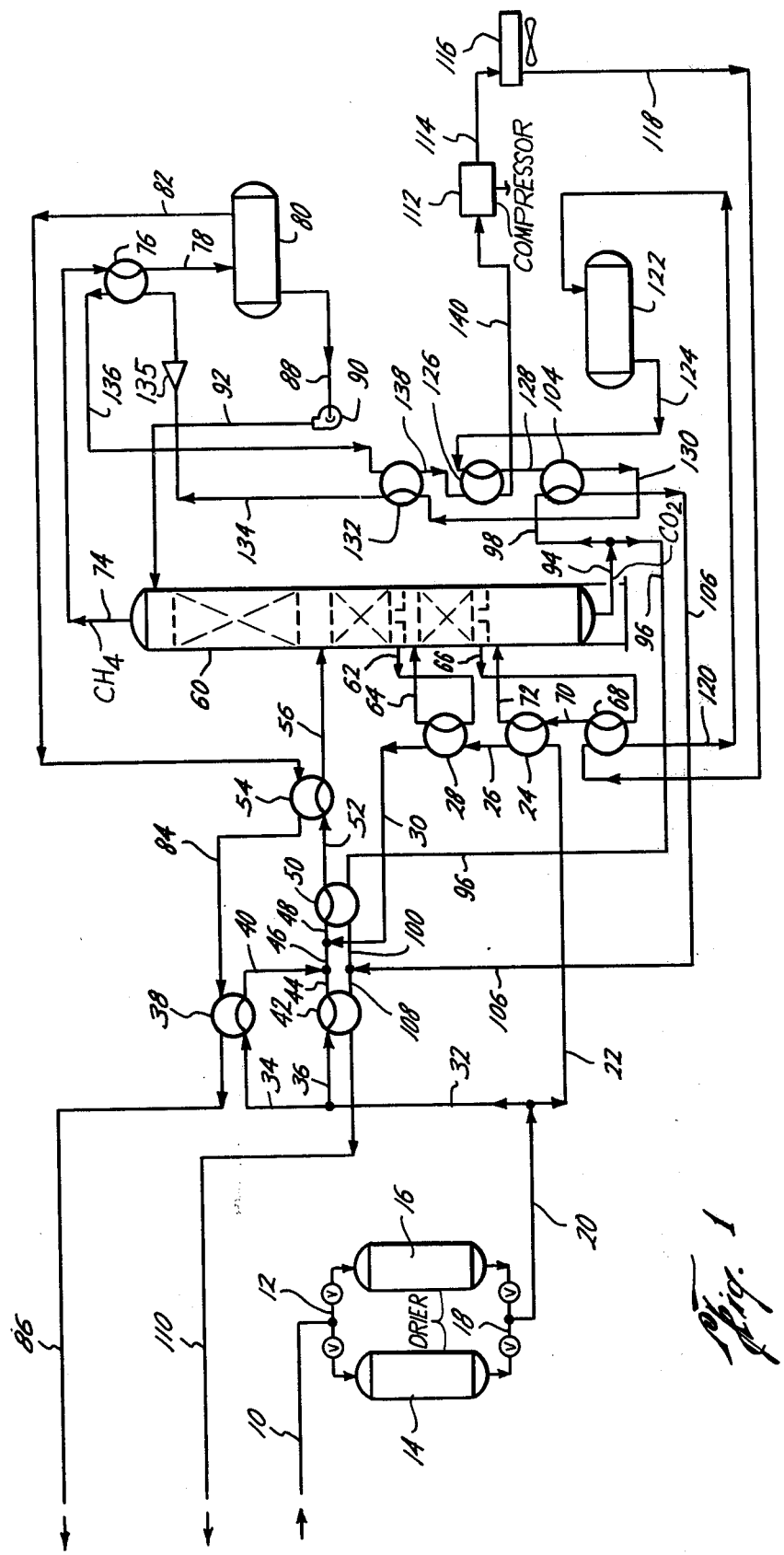
FIG. 1 is a schematic flow diagram showing a preferred embodiment of the method of this invention with common valves, fittings, gauges, and instrumentation, well known to those skilled in the art, omitted.

The method of this invention will be more completely described by referring to the attached drawings and the specific discussion thereof. Turning to FIG. 1, since temperatures and pressures are involved in this process whereby water would freeze, it is necessary that the gases be dry when subjected to the separation method of this invention. Therefore, if dry gases are not available, the gases enter through line 10, a manifold 12, and thence to molecular sieve dehydrators 14 and 16 wherein the gases are dried. As is well known to those skilled in the art, molecular sieve dehydrators are operated alternatively, one being regenerated while the other is removing water from the inlet gas. Though it is not shown in FIG. 1 it is necessary to provide a means for regenerating the molecular sieve, such regeneration means are well known to those of ordinary skill in the art.

The dried gas leaves molecular sieve 14 or 16 through manifold 18 and thence through line 20. The dried gas mixture, as stated before, may have a carbon dioxide content of from about 30 mol percent to about 90 mol percent with the balance of the gas being substantially methane, though some small amount of inert gas may be tolerated.

The gas enters the system at the ambient temperature of the gas, but to avoid freezing must be maintained at a pressure such that the gas mixture at no time approaches the triple point temperature for the composition of the gas mixture at any point in the system during the practice of the method. The locus of the triple point temperature is shown on FIG. 2 as line AB. It is preferred to operate the process of this invention at pressures from about 700 psia to about 1000 psia which, as seen from FIG. 2 as the temperature, avoids the triple point locus and thus avoids producing any solids. The lowest operating pressure possible is especially preferred, since it results in the most complete separation of the carbon dioxide from the methane. It is apparent from FIG. 2 that the lower the pressure at which the method of this invention is carried out, the more pure the product streams will be. However, the lower the pressure at which the method of this invention is carried out, the closer the conditions approach the conditions at which solid carbon dioxide will be formed.

The temperature at which the gas mixture is charged to the system effects only the amount of specific heat which must be removed in the method, and since heat exchange occurs, as will be later explained, with the exiting product streams, this need is easily balanced. As to operability, the separation of this invention is accomplished independently of the entering temperature of the mixed gases.

In order to achieve the most efficient separation with the least consumption of energy, it is preferable to split the feed gas stream in line 20 into separate streams for initial cooling. For purposes of discussion of the embodiment of this invention as shown in FIG. 1, it will be assumed that twenty million Standard Cubic Feet per Day (SCFD) inlet gas at a temperature of 120° F. and 765 psig pressure with a composition of 40 mol percent methane and 60 mol percent carbon dioxide is charged to the system. While the composition may vary as previously stated and the pressure selected as hereinbefore, the temperature of the inlet gases is of relatively minor importance except that such temperature of the inlet streams will cause a variation in the determination of the heat exchange loads for the various heat exchangers of the system. Once one of ordinary skill in the art is advised of the temperature and pressure involved and the composition of the gas and informed of the method of this invention, he will be able, through engineering calculations, to determine the proportions of the feed gas in line 20 to be divided through the various heat exchange means in the method. Preferably the feed stream 20 is divided into three heat exchange streams, or loops; for an initial cooling. The first precooling stream splits off line 20 as line 22 and thence to heat exchanger 24 where it is cooled with indirect heat exchange with a side stream drawn from the fractionating column to be described hereinafter. Heat exchanger 24 acts as a reboiler for the column as described hereinafter. The cooled gases exit heat exchanger 24 through line 26 and thus to heat exchanger 28, another side reboiler for the fractionating column operating in the same manner as heat exchanger 24, but at a lower temperature. The gases, further cooled, exit the side reboiler 28 through line 30 which conducts the cooled gases to join the other feed gas having been initially cooled.

The balance of the gases not taken off in the first initial cooling stream through line 22 is conducted through line 32 and split into two lines 34 and 36. The feed gas in line 34 forms a second precooling stream and receives its initial cooling in heat exchanger 38 through indirect heat exchange with the overhead stream from the fractionation vessel, or tower, containing methane with only a small amount of carbon dioxide. The gases thus cooled exit heat exchanger 38 through line 40 and are rejoined with the main gas stream ending the initial precooling of the second portion of the feed stream. The third portion of the feed stream, through line 36, enters heat exchanger 42 where it is cooled by indirect heat exchange with a portion of the carbon dioxide-rich bottoms product stream from the fractionating column as discussed hereinafter. The cooled gases exit exchanger 42 through line 44 where the gases are joined by the other two precooled gas streams. This junction can be accomplished in any acceptable order. In FIG. 1, for illustration only, the gases of line 44 are joined by the gases from line 40 in line 46 which then join the precooled gases from line 30 in line 48.

The separate streams, now recombined and cooled, are further cooled in heat exchanger 50 where they contact a portion of the bottoms stream from the fractionating column. The entire feed gas stream exits this heat exchanger 50 through line 52 and into heat exchanger 54 wherein they are further cooled by indirect heat exchange contact with the overhead product stream consisting essentially of methane with a small amount of carbon dioxide. The amount of carbon dioxide in the overhead stream, at its temperature and pressure, can be determined from FIG. 2. At the operating conditions of this embodiment, it contained about 5 mol percent carbon dioxide.

Figure 2:
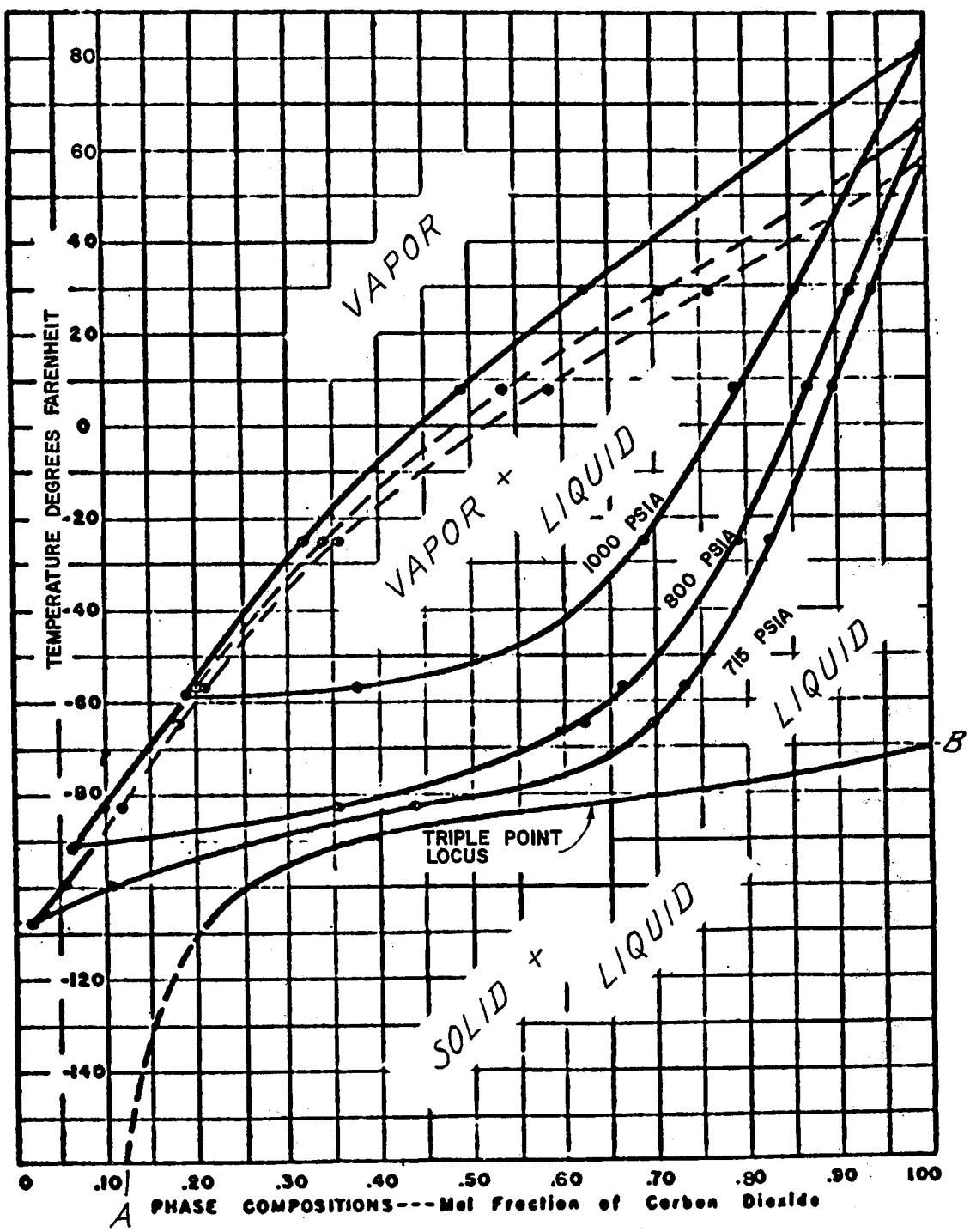
FIG. 2 is a graph showing the triple point temperature locus and the phases for a carbon dioxide-methane binary system.

The cooled gases exiting heat exchanger 54 through line 56 are now in condition for introduction into the fractionating column. In this particular example the condition of the gases is about −50° F. at a pressure of about 750 psia, and, as can be seen from FIG. 2, are well within the vapor-liquid region of the binary system. As such the gases can be readily separated through fractionation in the column 60 where the gaseous phase, mainly methane, rises and the bottoms, or liquid phase, migrates towards the bottom of the column 60. The fractionation vessel, or column 60, while preferably a packed column having sufficient theoretical stages for separation of the liquids and vapors, being designed using sound engineering principles known to those of ordinary skill in the art, is preferably packed with a suitable packing material such as saddles, palls, rings or the like, could be, if desired, a bubble plate column. In the practice of this particular embodiment, the fractionation vessel 60 contains about 35 feet of packing shown in separate beds with the internal diameter of about 36 inches. The column 60 in the practice of our invention receives the heat for its reboiler through heat exchange in the first initial preheat stream, partially, through the reboiler 28 which is fed by a portion of the liquids migrating downward through the column where it is drawn off in line 62 and conducted through heat exchanger 28 wherein the mixture from the column is heated while cooling the portion of the feed gases introduced into side boiler 28 through line 26. The warmed liquid is returned to the column 60 through line 64 where the separation of the gases from the liquid is enhanced by the heating. Preferably, the column 60 will have two side reboilers, it being understood that greater or fewer reboilers can be used, depending upon the degree of efficiency of separation desired and the initial composition of the gases introduced into the method of this invention. In FIG. 1, a preferred embodiment of the practice of our invention for the specific gas introduced into the system through line 10, vessel or column 60 has a second side stream withdrawn through line 66 thence to a reboiler/refrigerant condenser 68, to be further discussed later with respect to the refrigeration cycle, wherein the liquid removed from the column 60 is heated. The heated liquid exits the refrigerant condenser 68 through line 70 to the second side reboiler 24, discussed previously in connection with the initial precooling of the first portion of the feed stream, where the liquid stream is in indirect heat exchange with the gases entering the side reboiler 24 through line 22. This mixture, thus heated, exits the side reboiler 24 through line 72 and return to the column 60. In the practice of this specific embodiment the bottoms of the tower are present at a temperature of about 60° F. and a pressure of 725 psig.

Leaving the bottoms of the column 60 for a moment, the methane rich gas stream exits the top of the column 60 through line 74 at a temperature of about −95° F. and pressure of about 725 psig, to a reflux condenser 76 where a portion of the overhead stream is condensed through indirect heat exchange with the refrigeration cycle to be discussed hereinafter. The partially condensed overhead stream exits the condenser 76 through the line 78 to a reflux accumulator 80 operated, for this preferred embodiment at a temperature of about −100° F. and pressure of about 720 psig. While these conditions will vary for different inlet gas conditions, we have found it particularly advantageous for the use in the method of this invention. In the reflux accumulator 80 a portion of the overhead stream is flashed and exits as a gas through line 82. The overhead gas stream being rich in methane leaves the reflux accumulator 80 through line 82 and thence to heat exchanger 54 where the temperature of the product stream is raised by indirect heat exchange with the inlet gas streams prior to charging to the fractionating column 60.

The warmed product gases exit heat exchanger 54 through line 84 and thus to heat exchanger 38, in the second heat exchange loop, or stream, where the temperature of the product methane gas is further raised in the initial cooling loop of a portion of the inlet gas stream. The product gas thus exits heat exchanger 38 through line 86 at conditions of about 100° F. and 715 psig and is predominantly methane with small amounts of carbon dioxide, i.e., up to about 10 mol percent depending upon the feed gas involved, preferably up to about 5 mol percent. Conversely, "predominantly methane" is construed to mean about 90 mol percent methane or greater and, preferably about 95 mol percent methane, or greater. When these conditions are compared with the inlet conditions of the gas undergoing the separation process, it is readily seen that a highly efficient process results wherein the maximum energy has been removed from the outlet gases in the process of preparing the inlet gas for separation in the process of this invention. For this particular embodiment about 8.4 million SCFD containing about 95 mol percent methane and about 5 mol percent carbon dioxide is produced. Compared to the inlet gas streams, heating value of 364 British Thermal Unit per Square Cubic Foot (BTU/SCF), this product gas had a heating value of about 857 BTU/SCF (pure methane is 911 BTU/SCF).

Returning now to the reflux accumulator 80, the liquid reflux stream exits the accumulator 80 through line 88 and thence to pump 90 and through line 92 where it is reintroduced into the column 60 to improve the degree of separation of the two components of the inlet gas in this preferred embodiment of this invention. As can be seen from FIG. 2 the reflux stream would contain approximately 10 mol percent carbon dioxide while the overhead streams for these particular conditions would contain only about 5 mol percent. Thus, the efficiency of the method is greatly improved by the recycling of the reflux stream.

The liquid bottoms stream removed from the column 60, rich in carbon dioxide, exits through line 94 as a liquid at conditions of about 725 psig and 60° F. As stated hereinbefore these conditions will vary with respect to the various feed mixtures involved, but are given here for this specific inlet gas to aid one of ordinary skill in the art to arrive at the calculations needed for adjusting the system to other conditions, which can be done using engineering calculations once the method of this invention is known. The liquid carbon dioxide in line 94 is split into two lines 96 and 98. The portion of the liquid stream in line 96 is introduced at substantially reduced pressure and temperature into heat exchanger 50 where the partially cooled portions of the inlet gas stream having been reunited are further cooled. This stream being now partially flashed in heat exchanger 50 at the substantially reduced pressure exits at an increased temperature through line 100 and is joined by the other bottoms stream. The other portion of the bottoms stream containing substantially pure carbon dioxide exiting line 94 through line 98 enters heat exchanger 104 at substantially reduced pressure and temperature where it is partially flashed by heat from the refrigerant cycle to be discussed hereinafter. The vapor and liquid mixture of carbon dioxide being at reduced pressure and somewhat higher temperature exits the heat exchanger 104 through line 106 and thence to join the other bottoms stream 100, exiting heat exchanger 50, in line 108 and thence introduced into heat exchanger 42 wherein the liquid gas mixtures containing substantially pure carbon dioxide are further flashed into the gaseous state to take advantage of the heat of vaporization of the carbon dioxide in the initial cooling of the portion of the inlet gas stream in the third pre-cooling loop in heat exchanger 42. Thus, the gases exit exchanger 42 in line 110 as a product gas consisting essentially of carbon dioxide and having conditions of about 100° F. and 75 psig. This stream contains, in the practice of this preferred embodiment, approximately 99 mol percent carbon dioxide with only 1 mol percent methane, and in this illustrative embodiment is 11.6 million SCFD of product. Of course, greater separation can be obtained by a finer tuned operating of the above described method, this discussion being merely an example of the method of this invention. While achieving 99 mol percent or greater carbon dioxide in the product stream 110 is preferred, it is considered, for purposes of this invention, that higher amounts of methane may be present in certain situations with the carbon dioxide content being about 95 mol percent or greater.

Now to discuss the refrigerant loop. This refrigerant loop is necessary only to overcome the inefficiency of heat exchange and in this particular embodiment of this invention provides the cooling to condense the gases in the reflux overhead, thus producing a more efficient separation of the gases. The refrigerant may be any acceptable refrigerant which will operate at the above-described conditions. For this particular operation, ethane has been selected as the preferred refrigerant. Certainly, there are certain halogenated hydrocarbons which would be acceptable for the practice of this invention.

The ethane is compressed in a refrigerant compressor 112 to increase the pressure of the refrigerant to about 600 psig for use in the operation of this particular embodiment of the invention. The compressed refrigerant exits through line 114 and thence to a refrigerant cooler 116 which preferably is an air cooler with the ability to cool the refrigerant vapor to nearly ambient temperature. The cooled, compressed refrigerant exits the air cooler 116 through line 118 and thence to reboiler/refrigerant condenser 68 wherein some of the heat of condensation of the refrigerant is passed to the liquid stream from the fractionation vessel 60. The refrigerant, now further cooled and totally condensed exits the reboiler/refrigerant condenser 68 through line 120 and thence to the refrigerant surge tank 122 wherein the refrigerant is at about 580 psig and 75° F. The liquid refrigerant exits the surge tank 122 through line 124 and thence to heat exchanger 126 wherein the refrigerant liquid is cooled in indirect heat exchange while heating heat the return stream of refrigerant vapor to the compressor as will be discussed hereinafter. The cooled refrigerant exits heat exchanger 126 through line 128 to the refrigerant/bottoms stream heat exchanger 104 where the liquid refrigerant is further cooled by the flashing of the carbon dioxide bottoms product entering through line 98. The cooled refrigerant exits heat exchanger 104 through line 130 and is thence introduced into the heat exchanger 132 where the liquid is still further cooled through indirect heat exchange with refrigerant as will be discussed hereinafter. The cooled refrigerant exits heat exchanger 132 through line 134 and thence to the reflux condenser 76 at substantially reduced pressure and temperature where it is totally flashed, removing heat from the overhead stream of the column causing it to partially condense and thence pass to the reflux accumulator 80. Of course, it will be understood that the flashing could be accomplished through an expander valve 135 prior to introducing the refrigerant into the reflux condenser 76. The flashed refrigerant exits the reflux condenser 76 through line 136 and returns to heat exchanger 132 where it is warmed through indirect heat exchange with the liquid refrigerant. The gaseous refrigerant exits the heat exchanger 132 through line 138 and is further warmed in heat exchanger 126 by indirect heat exchange with refrigerant vapors from line 124. It then exits heat exchanger 126 through line 140 and completes the refrigerant loop by entering the ethane refrigerant compressor 112 at approximately 20 psig, for this embodiment. The heat exchanger 132 and 126 serve to minimize the amount of refrigerant needed improving the efficiency of the method. The skilled engineer, in designing a particular application of this invention will recognize that liquid must not condense in the compressor 122.

In the preferred embodiment hereinbefore described a three stage compressor having a brake horsepower of approximately 1000 was considered to be adequate for the fine separation accomplished. Of course, those of ordinary skill in the art would readily understand that additional compressor brake horsepower and design depends upon the inlet conditions of the gases involved and the refrigerant of choice.

To illustrate the improvement, and high efficiency of the foregoing system, the energy requirements to raise the heating value of the contained methane is compared with an amine absorption process applied to the same system. As state previously, the 20 million SCFD inlet gas had a heating value of 364 BTU/SCF and after processing the 8.4 million SCFD overhead product gas, containing 95% methane and 5% carbon dioxide, had a heating value of 857 BTU/SCF. External power to run the reflux pump 90, the compressor 112 and the fan on the air cooler 116, the total external energy requirements, required 1016 brake horsepower which, when added to the requirements for drying the gas required about 5 BTU/SCF of inlet gas.

An amine system, at an abnormally high loading of 5.5 SCF carbon dioxide per gallon of amine, for example, monoethanolamine, would require about 114 BTU/SCF of inlet gas to regenerate the absorbent alone and a total of 119 BTU/SCF considering fans, pumps and the like. At a more normal loading of 3.5 SCF of carbon dioxide per gallon, the requirement would be about 170 BTU/SCF of inlet gas, almost 50% of the recoverable energy in the mixture.

The above calculations are made without considering the efficiencies in motors, pumps, and other extraneous equipment in either case. Therefore, the calculations are representative of the surprisingly efficient operation of the method of this invention and the advantageous results achieved thereby.

It can readily be seen from the foregoing discussion that the method of our invention accomplishes a substantial separation of carbon dioxide and methane, even at high carbon dioxide levels, with a highly efficient system which consumes a minimum of energy. Many modifications and adjustments of the above-described method may be made by those of ordinary skill in the art after having read the above discussion hereof. Accordingly, any such modifications or changes are considered to be within the scope of this invention.

We claim as our invention:

1. A method for the separation of carbon dioxide from methane in a dried gas mixture wherein the carbon dioxide is from about 30 mol percent to about 90 mol percent of the gas mixture which comprises:
    (a) cooling the gas mixture to form a vapor-liquid binary system by dividing the mixture into three streams for partial cooling and recombining the streams for further cooling by heat exchange with the product streams of a fractionation step wherein a first stream is partially cooled by indirect heat exchange with a liquid side stream from the fractionation step; a second stream is partially cooled by indirect heat exchange with the overhead product stream from the fractionation step; and a third stream is partially cooled by indirect heat exchange with the bottoms product stream of the fractionation step prior to recombining the streams for further cooling;
    (b) fractionating the binary system to remove an overhead stream comprising predominately methane in the gaseous phase and a bottoms streams consisting essentially of carbon dioxide in the liquid phase;
    (c) warming the overhead and bottoms streams from the fractionating step through indirect heat exchange with inlet gas to cool the inlet gas (step a);

provided that the entire method is performed, without formation of solids, at a pressure below the critical pressure and a temperature above the triple point for the carbon dioxide-methane mixture.

2. A method for the separation of carbon dioxide from methane in a gas mixture, wherein the carbon dioxide is present in amounts of from about 30 mol percent to about 90 mol percent in the gas mixture, which comprises:
    (a) drying the gas mixture;
    (b) separating the gas mixture into three streams for precooling;
    (c) cooling the three streams by:
        (i) indirect heat exchange of a first precooling stream with a side stream of liquid from a fractionation step (f);
        (ii) indirect heat exchange of a second precooling stream with a bottoms product stream from the fractionation step (f); and
        (iii) indirect heat exchange of a third precooling stream with an overhead product stream from the fractionation step (f);
    (d) combining the precooled streams;
    (e) cooling the combined streams by indirect heat exchange with the product streams, such cooling to form a vapor-liquid binary system;
    (f) fractionating the binary system in a fractionation vessel, supplying heat to said vessel by indirect heat exchange with the first precooling stream of the gas mixture;
    (g) recovering as an overhead product a gas stream being predominantly methane, a portion of which overhead stream is condensed and returned to the fractionation vessel as a reflux stream;
    (h) recovering as a bottoms product a liquid stream consisting essentially of carbon dioxide and a small amount of methane; and
    (i) heating the product streams by indirect heat exchange with the gas mixture to take advantage of the energy present to reduce the temperature of the gas mixture;

provided, that the above steps are performed without formation of solids and such that the gas mixture and vapor-liquid binary system remains at a pressure below the critical pressure and at a temperature above the triple point temperature of the gas mixture.

3. The method of claim 2 wherein a refrigeration cycle is used to remove heat from the overhead product stream to produce a reflux stream and to add heat to a side stream from the fractionation step.

* * * * *